(12) United States Patent
Taugerbeck et al.

(10) Patent No.: US 8,133,887 B2
(45) Date of Patent: Mar. 13, 2012

(54) OXAPHENANTHRENE DERIVATIVES

(75) Inventors: Andreas Taugerbeck, Darmstadt (DE); Detlef Pauluth, Ober-Ramstadt (DE); Beate Kretschmer, Koenigstein (DE); Hanns Wurziger, Darmstadt (DE); Axel Jansen, Darmstadt (DE); David Maillard, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 870 days.

(21) Appl. No.: 12/158,396

(22) PCT Filed: Nov. 29, 2006

(86) PCT No.: PCT/EP2006/011457
§ 371 (c)(1),
(2), (4) Date: Jun. 20, 2008

(87) PCT Pub. No.: WO2007/079830
PCT Pub. Date: Jul. 19, 2007

(65) Prior Publication Data
US 2008/0312224 A1  Dec. 18, 2008

(30) Foreign Application Priority Data
Dec. 22, 2005 (DE) .................. 10 2005 062 098

(51) Int. Cl.
*A61K 31/5377* (2006.01)
*A61K 31/352* (2006.01)
*C07D 405/12* (2006.01)
*C07D 413/12* (2006.01)
*C07D 311/80* (2006.01)

(52) U.S. Cl. ............ 514/232.8; 514/320; 514/454; 544/150; 546/196; 549/390

(58) Field of Classification Search .......... 549/390, 549/391; 514/454, 232.8, 320; 544/150; 546/196
See application file for complete search history.

(56) References Cited

U.S. PATENT DOCUMENTS
7,326,447 B2 * 2/2008 Taugerbeck et al. ......... 428/1.1
7,824,745 B2 * 11/2010 Taugerbeck et al. ......... 428/1.1

FOREIGN PATENT DOCUMENTS
DE  10 2004 004228 A1  9/2004
JP  2005 120073 A  *  5/2005

OTHER PUBLICATIONS

Rog, D.J. et al., "Randomized, Controlled Trial of Cannabis-Based Medicine in Central Pain in Multiple Sclerosis," Neurology, Sep. 2005, pp. 812-819, XP002423046.

* cited by examiner

*Primary Examiner* — Bernard Dentz
(74) *Attorney, Agent, or Firm* — Millen, White, Zelano & Branigan, P.C.

(57) ABSTRACT

The invention relates to compounds of the formula (I), in which $R^1$, $R^2$, $R^3$, $R^4$, Y and A have the meanings indicated, and to processes for the preparation thereof and to the use thereof for the preparation of medicaments.

(I)

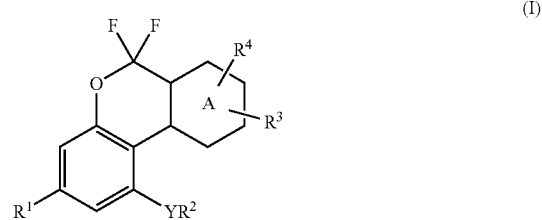

18 Claims, 2 Drawing Sheets

OXAPHENANTHRENE DERIVATIVES

This application claims the benefit of International Application No. PCT/EP2006/0011457, filed Nov. 29, 2006.

The invention relates to compounds of the formula I

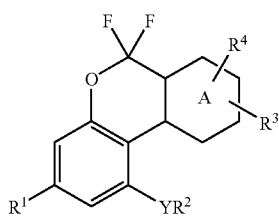

in which
A denotes a saturated, unsaturated or aromatic carbocyclic or heterocyclic radical having 6 ring members, in which, in the case of saturated radicals, one or more $CH_2$ groups may be replaced by CO,
$R^1$, $R^2$,
$R^3$, $R^4$, independently of one another, denote H, Hal, branched or un-branched alkyl having 1 to 12 C atoms, in which, in addition, one or more H atoms may be replaced by F, one or more $CH_2$ groups may be replaced by —C=C—, —C≡C—, C=O, —O—, —S—, —NH—, —$NR^1$— or substituted or unsubstituted phenylene, and one or more $CH_3$ groups may be replaced by

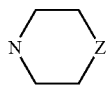

in which z denotes $CHR^5$, S, O, $NR^5$ or $NR^5$,
Hal denotes fluorine, chlorine, bromine or iodine,
Y denotes a single bond, O, S or $NR^5$;
$R^5$, denotes H or alkyl,
and physiologically acceptable salts and solvates, stereoisomers thereof and mixtures thereof in all ratios.

Owing to asymmetrically substituted carbon atoms, compounds of the formula I can exist as stereoisomers. The invention therefore relates to all isomers, both in pure form, as the racemate and also as a mixture of diastereomers or enantiomers.

The invention had the object of finding and optimising inhibitors of cannabinoid receptors (CB receptors). The present invention relates to novel therapeutic and/or prophylactic uses of compounds which inhibit CB receptors, and to pharmaceutical compositions which comprise one or more of these compounds as an active component. The compounds mentioned in this invention exhibit CB receptor-inhibiting properties and may be of outstanding importance for novel medical applications.

Cannabinoids occur in the Indian hemp plant *Cannabis Sativa* L. and have been utilised for centuries for medical use (Mechoulam, R.; Feigenbaum, J. *J. Prog. Med. Chem.* 1987, 24, 159). However, the research in the area of cannabinoids only brought crucial information on CB receptors to light in the last decade. The discovery and cloning of two cannabinoid receptor subtypes (CB1 and CB2) stimulated the search for novel cannabinoid receptor antagonists (Munro, S.; Thomas, K. L.; Abu-Shaar, M. *Nature* 1993, 365, 61. Matsuda, L. A.; Bonner, T. I. *Cannabinoid Receptors*, Pertwee, R. G. Ed. 1995, 117, Academic Press, London). In addition, the pharmaceutical industry started to become interested in the development of cannabinoid medicaments for the treatment of diseases associated with disorders of the cannabinoid system. The wide spread of the CB1 receptor in the brain, in combination with the strictly peripheral localisation of the CB2 receptor, made the CB1 receptor a very interesting molecular target for CNS-directed active compound development. In particular, the compounds according to the invention have CB1 receptor activity and can be employed for the treatment of psychiatric diseases, such as psychoses, anxiety disorders, depression, aprosexia, memory disorders, cognitive disorders, loss of appetite, obesity, addiction, drug dependence and neurological disorders, such as neurodegenerative processes, dementia, dystonia, muscle spasms, tremor, epilepsy, multiple sclerosis, traumatic brain injuries, strokes, Parkinson's, Alzheimer's, Huntington's disease, Tourette's syndrome, cerebral ischaemia, cerebral apoplexy, craniocerebral trauma, spinal cord injuries, neuroinflammatory diseases, cerebral arteriosclerosis, viral encephalitis, diseases associated with demyelinisation, and for the treatment of pain diseases, including neuropathic pain diseases, and other diseases in which cannabinoid neurotransmission plays a role, including septic shock, glaucoma, cancer, diabetes, vomiting, nausea, asthma, respiratory tract diseases, gastrointestinal diseases, gastric ulcer, diarrhoea and cardiovascular diseases.

Surprisingly, it has now been found that THC derivatives ($\Delta^9$-tetrahydrocannabinol derivatives) in which the geminal methyl groups on C9 have been replaced by fluorine develop improved pharmacological actions, but without pronounced psychoactivity. To date, similar compounds were only known for their liquid-crystalline properties (JP2005120073; DE102004004228).

The compounds can furthermore act on muscarinic receptors. In addition, it has been found that the compounds of the formula I and salts thereof, which are important intermediates for the preparation of medicaments—in particular those which act, for example, on the central nervous system—can be obtained by reaction of compounds of the formula II or salts thereof with compounds of the formula III or salts thereof.

Above and below, the radicals $R^1$ to $R^5$, ring A, Y and Hal have the meanings indicated for formula I, unless expressly indicated otherwise.

The alkyl radical preferably denotes unbranched or branched alkyl and has 1 to 12, preferably 1 to 8, C atoms. Alkyl therefore denotes, in particular, for example, methyl, ethyl, n-propyl, isopropyl, n-butyl, sec-butyl or tert-butyl, furthermore also pentyl, 1-, 2- or 3-methylbutyl, 1,1-, 1,2- or 2,2-dimethyl-propyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Preference is also given to alkyl radicals in which one $CH_2$ group may be replaced by an O or S atom or by a CH=CH group, or at least one H atom may be replaced by F. The alkyl radical preferably denotes a radical of the following sub-formula: $C(CH_3)_2$-Alk, where Alk denotes a preferably straight-chain alkyl radical having 1 to 7 C atoms.

The ring A preferably denotes a saturated or unsaturated carbocyclic or heterocyclic radical having 6 ring members, where, in the case of a heterocyclic radical, 1 to 4 heteroatoms selected from N, S and 0 may be present. The ring A denotes, in particular, for example, cyclohexane, in which, in addition, one $CH_2$ group may be replaced by CO, cyclohexene or piperidine.

Hal denotes fluorine, chlorine, bromine or iodine, in particular fluorine.

$R^1$ denotes unbranched or branched alkyl and has 1 to 12, preferably 3 to 10, C atoms and in particular 5 to 9 C atoms. $R^1$ preferably denotes n-pentyl, 1,1-dimethylheptyl or 1,2-dimethylheptyl.

$R^2$ preferably denotes H, alkyl or

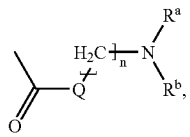

in which
n denotes 1, 2, 3, 4, 5, 6, 7, 8, 9, 10, 11 or 12
Q denotes O, NH, N-alkyl or $CH_2$,
$R^a$, $R^b$ independently denote H or alkyl
or the $NR^aR^b$ group together also denotes

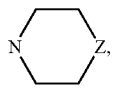

in which
Z denotes $CH_2$, S, O, $NR^1$ or NH.

$R^2$ denotes, in particular, one of the following groups:

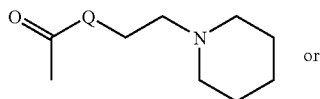 or

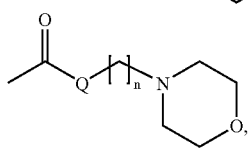

in which n and Q have the meaning mentioned above.

$R^3$, $R^4$ denote, independently of one another, in particular, H, methyl, alk-2-yn-1yl or alk-2-en-1-yl having 3 to 8 C atoms, or $R^3$ and $R^4$ together denote carbonyl oxygen.

$R^3$ and $R^4$ particularly preferably denote, independently of one another, H, but-2-yn-1-yl or pent-2-yn-1-yl.

$R^5$ preferably denotes H, methyl or ethyl.

Y preferably denotes O, S or $NR^5$, where $R^5$ has the meaning mentioned above. Y particularly preferably denotes O.

The following compounds I1 to I39 and Ia according to the invention are very particularly preferred:

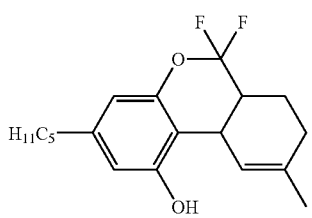
I1

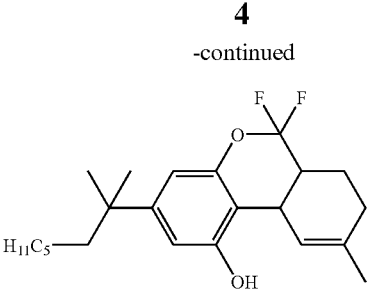
I2

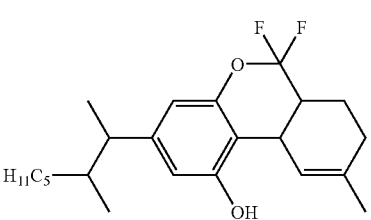
I3

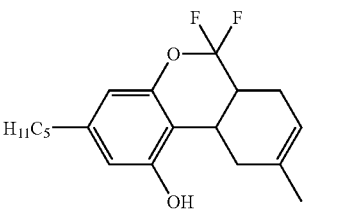
I4

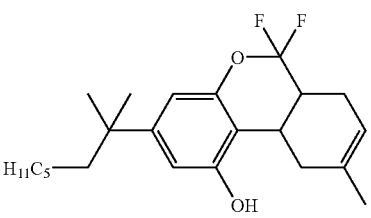
I5

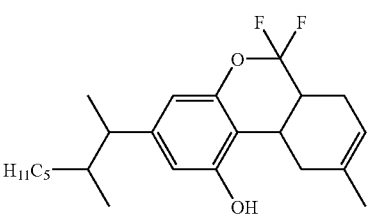
I6

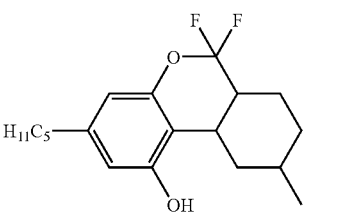
I7

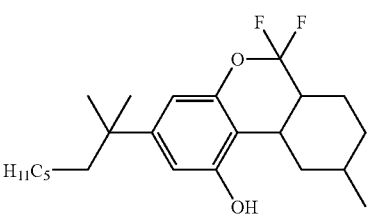
I8

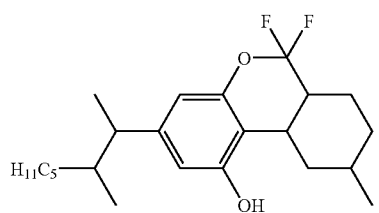
I9
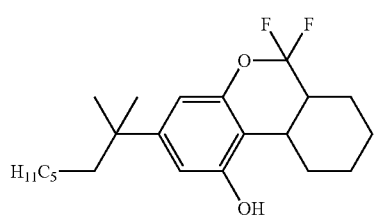
I10
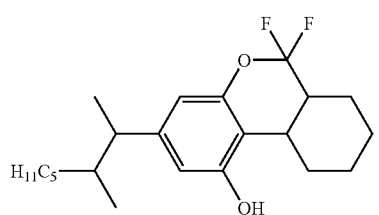
I11
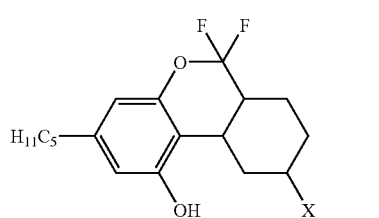
I12
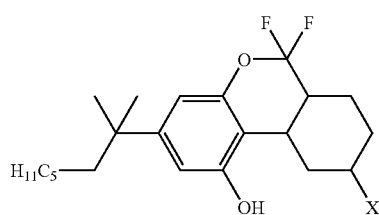
I13
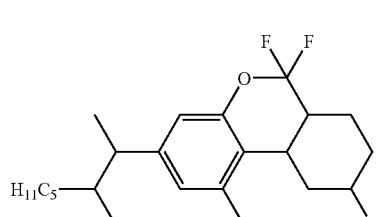
I14
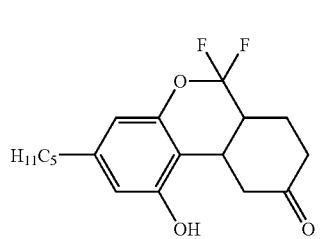
I15
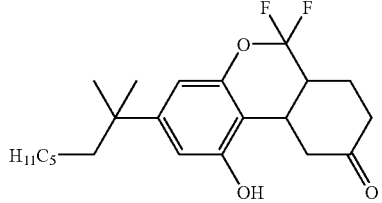
I16
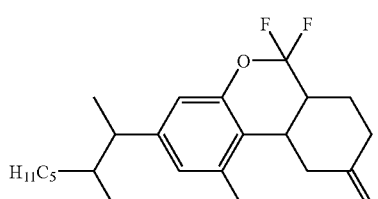
I17
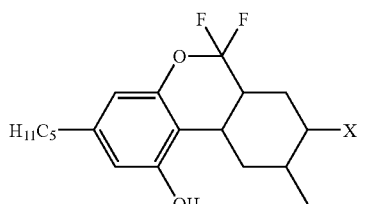
I18
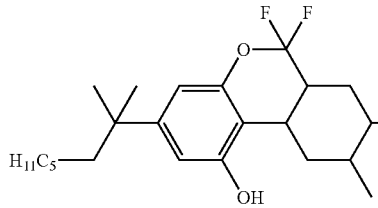
I19
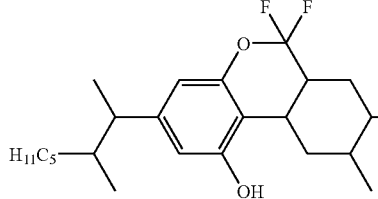
I20
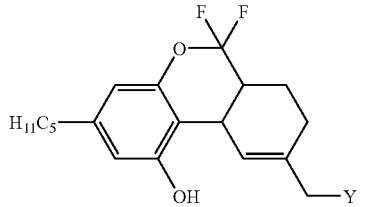
I21
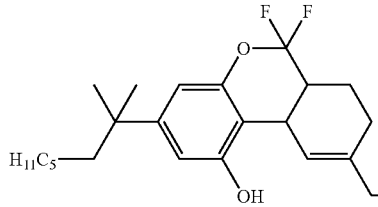
I22

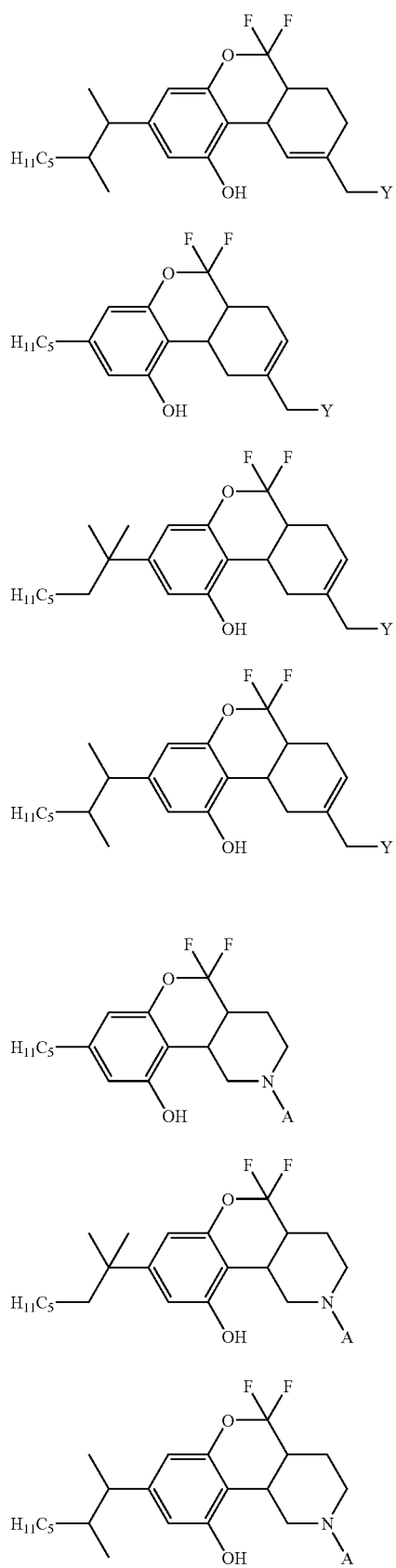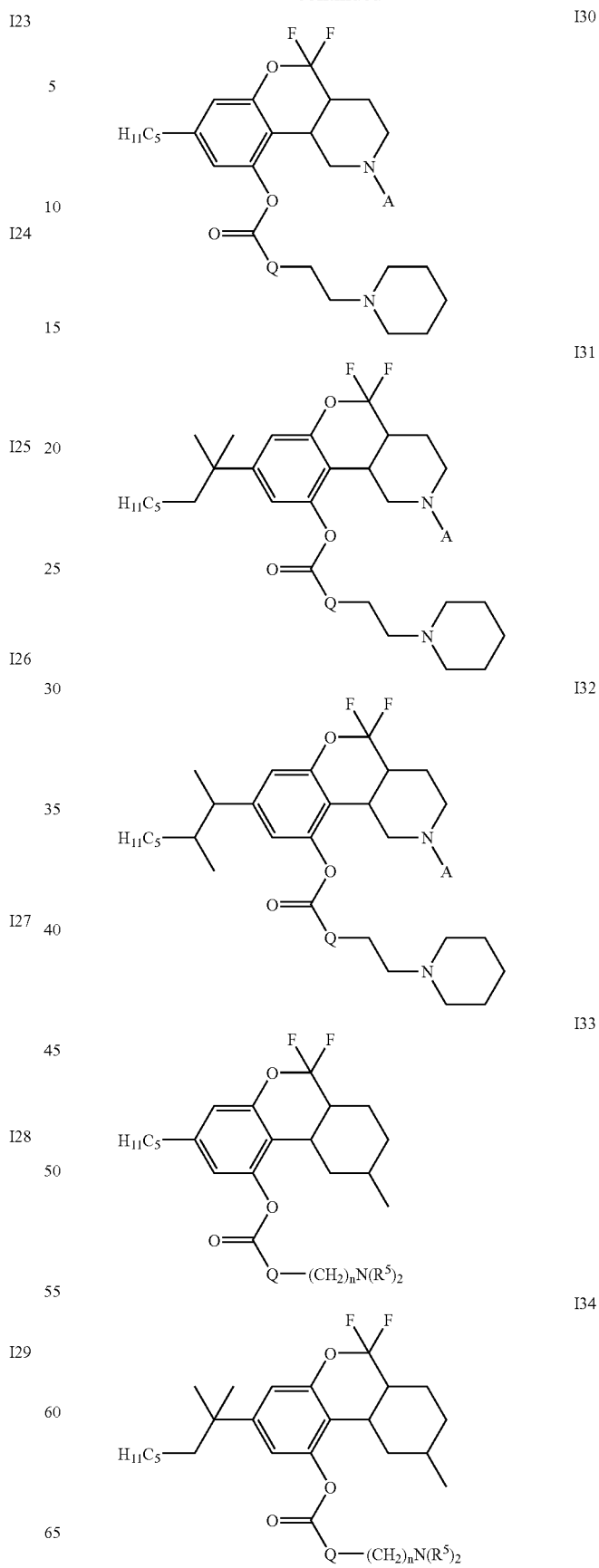

-continued

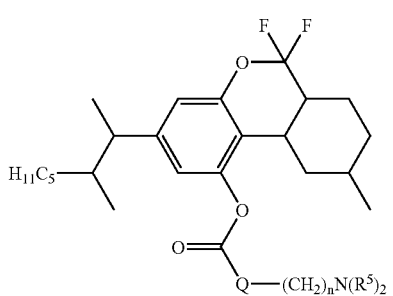

I35

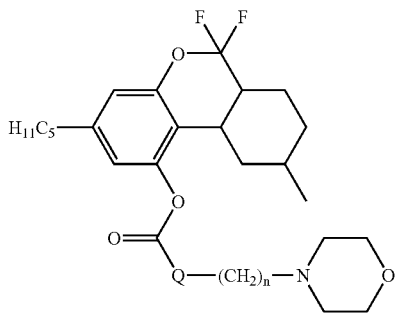

I36

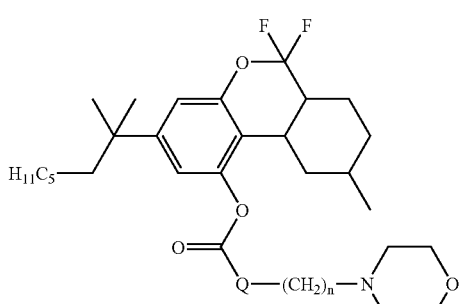

I37

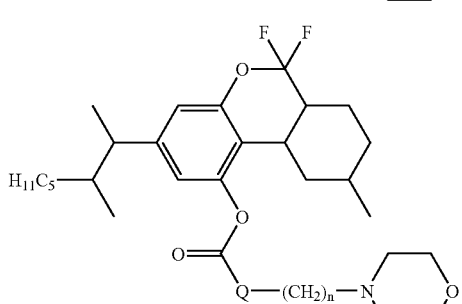

I38

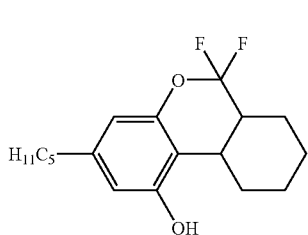

Ia where
x denotes OH, O-alkyl, N(R$^5$)$_2$
Y denotes OH, O-alkyl, COOR$^5$ or CON(R$^5$)$_2$
and
A denotes NHCH$_2$C≡C—R$^5$ or NHCH$_2$HC═CH—R$^5$
and R$^5$ and Q have the meanings indicated above.

The invention additionally relates to processes for the preparation of compounds of the formula I in accordance with the following scheme:

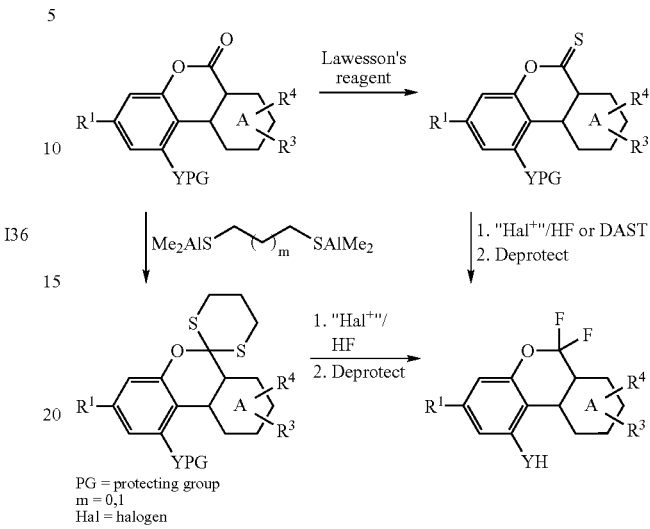

PG = protecting group
m = 0,1
Hal = halogen

The starting compounds for the process according to the invention are the compounds of the formula II

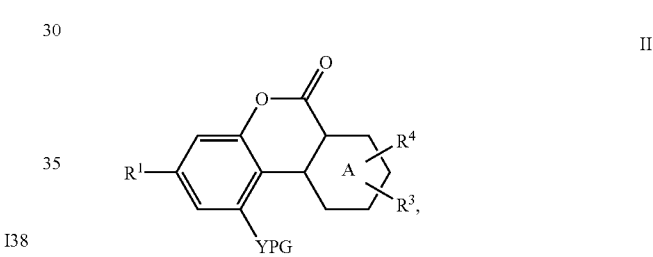

II where R$^1$, R$^3$, R$^4$ and Y are selected corresponding to the end compounds of the formula I, and PG denotes a protecting group, for example an ester- or amide-forming group, such as trialkylsilyl, alkylcarbonyl group or benzyl and in particular trimethylsilyl, acetyl, or benzyl.

The present invention also relates to the novel compounds of the formula II.

The invention thus relates to a process for the preparation of compounds of the formula I by reaction of compounds of the formula II, characterised by the following steps:

a) Reaction of the compounds of the formula II with aa) a thionation reagent, such as, for example, Lawesson's reagent, or ab) with a compound of the formula (alkyl)$_2$Al—S—(CH$_2$)$_m$—S—Al(alkyl)$_2$, in which alkyl preferably denotes methyl, ethyl, n-propyl, isopropyl, n-butyl, sec-butyl or tert-butyl and in particular methyl, and m denotes 2 or 3.

b) Oxidative fluorination of the compounds obtained in aa) or ab) using an oxidant which liberates halonium equivalents, such as, for example, 1,3-dibromo-5,5-dimethylhydantoin (DBH) or N-iodosuccinimide, in the presence of a fluoride source, such as, for example, triethylamine*3HF, or by reaction of the thionolactones obtained in ab) with fluorinating reagents, such as, for example, diethylaminosulfur trifluoride or DEOXOFLUOR®, which is bis(2-methoxyethyl)aminosulfur trifluoride, etc.; and subsequent deprotection to give the compounds of the formula I.

The invention furthermore relates to a process for the preparation of compounds of the formula I in accordance with the following scheme:

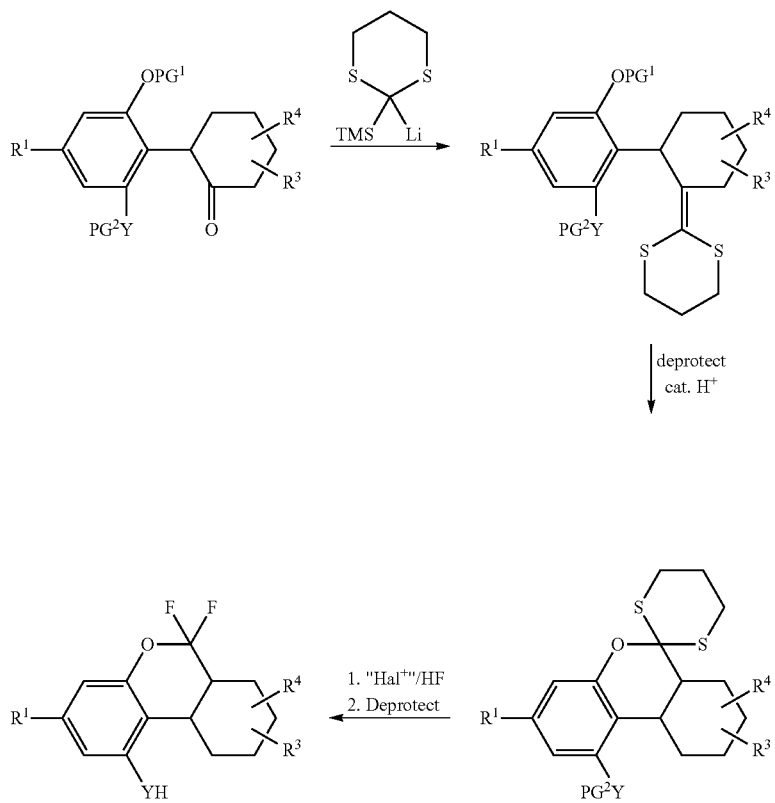

in which R¹, R³, and R⁴ is selected corresponding to the end compounds of the formula I.

The invention thus relates to a process for the preparation of compounds of the formula I, characterised by the following steps:

a) reaction of a compound of the formula III

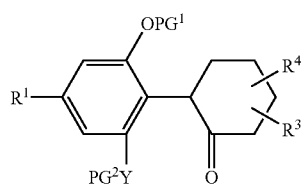

III in which $R^1$, $R^3$, and $R^4$ have the meaning indicated above, with a compound of the following formula

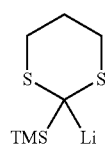

oxidative fluorination of the compounds obtained in a) using an oxidant which liberates halonium equivalents, such as, for example, 1,3-dibromo-5,5-dimethylhydantoin (DBH) or N-iodosuccinimide, in the presence of a fluoride source, such as, for example, triethylamine*3HF, and subsequent deprotection to give the compounds of the formula I.

Isomers can be separated by chromatography or crystallisation.

The reactions are generally carried out in an inert solvent.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Leaving groups are preferably Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart;).

Activated esters are advantageously formed in situ, for example by addition of HOBt or N-hydroxysuccinimide. The reaction is generally carried out in an inert solvent, in the presence of an acid-binding agent, preferably an organic base, such as DIPEA, triethylamine, dimethylaniline, pyridine, N-methylmorpholine, or quinoline, or an excess of the carboxyl component to be reacted. The addition of an alkali or alkaline-earth metal hydroxide, carbonate or bicarbonate or another salt of a weak acid or the alkali or alkaline-earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Suitable inert solvents are those mentioned above.

Compounds of the formula I can furthermore be obtained by liberating compounds of the formula I from one of the functional derivatives thereof, for example derivatives containing protecting groups, by treatment with a solvolysing or hydrogenolysing agent.

Preferred starting materials for the solvolysis or hydrogenolysis are those which otherwise conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group and/or those which carry a hydroxyl-protecting group instead of the H atom of a hydroxyl group, for example those which conform to the formula I, but carry a —COOR" group, in which R" denotes a hydroxyl-protecting group, instead of a —COOH group.

Preferred starting materials are also the oxadiazole derivatives, which can be converted into the corresponding amidino compounds.

It is also possible for a plurality of—identical or different—protected amino and/or hydroxyl groups to be present in the molecule of the starting material. If the protecting groups present are different from one another, they can in many cases be cleaved off selectively.

The expression "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1-20, in particular 1-8, C atoms. The expression "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl, butyryl; aralkanoyl, such as phenylacetyl; aroyl, such as benzoyl or tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl), 2-iodoethoxycarbonyl; aralkoxycarbonyl, such as CBZ ("carbobenzoxy"), 4-methoxybenzyloxy-carbonyl, FMOC; arylsulfonyl, such as Mtr. Preferred amino-protecting groups are BOC and Mtr, furthermore CBZ, Fmoc, benzyl and acetyl.

The expression "hydroxyl-protecting group" is likewise known in general terms and relates to groups which are suitable for protecting a hydroxyl group against chemical reactions, but which are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups is not crucial since they are removed again after the desired chemical reaction or reaction sequence; preference is given to groups having 1-20, in particular 1-10, C atoms. Examples of hydroxyl-protecting groups are, inter alia, benzyl, 4-methoxybenzyl, p-nitro-benzoyl, p-toluenesulfonyl, tert-butyl and acetyl, where benzyl and tert-butyl are particularly preferred.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut and Mtr groups can, for example, preferably be cleaved off using TFA in dichloromethane or using approximately 3 to 5 N HCl in dioxane at 15-30°, the FMOC group can be cleaved off using an approximately 5 to 50% solution of dimethylamine, diethylamine or piperidine in DMF at 15-30°.

Hydrogenolytically removable protecting groups (for example CBZ, benzyl or the liberation of the amidino group from its oxadiazole derivative)) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, trifluoro-methylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitro-benzene; esters, such as ethyl acetate, or mixtures of the said solvents.

Esters can be saponified, for example, using acetic acid or using NaOH or KOH in water, water/THF or water/dioxane, at temperatures between 0 and 100°.

Furthermore, free amino groups can be acylated in a conventional manner using an acid chloride or anhydride or alkylated using an unsubstituted or substituted alkyl halide, or reacted with $CH_3$—C($=$NH)—OEt, advantageously in an inert solvent, such as dichloromethane or THF, and/or in the presence of a base, such as triethylamine or pyridine, at temperatures between −60 and +30°.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline-earth metal salts, using bases (for example sodium hydroxide or carbonate or potassium hydroxide or carbonate) or into the corresponding ammonium salts. It is also possible to use physiologically acceptable organic bases, such as, for example, ethanolamine.

Owing to their molecular structure, compounds of the formula I according to the invention may be chiral and can accordingly occur in various enantiomeric forms. They can therefore exist in racemic or in optically active form.

Since the pharmaceutical efficacy of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Suitable resolving agents are, for example, optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline) or the various optically active camphorsulfonic acids. Also advantageous is chromatographic enantiomer separation with the aid of an optically active resolving agent (for example dinitrobenzoyl-phenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention encompasses not only the said compounds, but also mixtures and compositions which, besides these compounds according to the invention, also comprise other pharmacological active compounds or adjuvants which are able to influence the primary pharmacological action of the compounds according to the invention in the desired manner.

The compounds according to the invention can be employed as medicament active compounds in human or veterinary medicine, in particular for the prophylaxis or therapy of diseases which can be influenced by the central-nervous action of the compounds.

The compounds according to the invention can particularly preferably be employed for treating sexual disorders or increasing sexual performance, diarrhoea, nicotine dependence, inflammatory CNS diseases (demyelination, viral meningitis, multiple sclerosis, Guillain-Barré syndrome) and accident-induced brain injuries or head trauma, appetence disorders, i.e. dependences of various types (drugs, alcohol, sugar), bulimia and any consequences thereof (obesity, diabetes).

They are furthermore effective against hypertension or act against anxiety states and/or depression, as sedative, tranquilliser, analgesic, antiemetic or they have an inflammation-inhibiting action.

The central-nervous action can be demonstrated by administration to rats in doses of 0.1-1000 mg/kg, preferably of 1-100 mg/kg. Effects such as reduced spontaneous motor activity are observed, where the requisite dose depends both on the efficacy of the compound and also on the body weight of the experimental animal.

The invention accordingly relates to compounds of the formulae defined above and below and in the claims, including physiologically acceptable salts thereof, as medicaments, diagnostic agents or reagents.

The invention also relates to corresponding pharmaceutical compositions which comprise at least one medicament of the formula I and optionally excipients and/or adjuvants. Suitable excipients are organic or inorganic substances which are suitable for enteral (for example oral), parenteral or topical administration or for administration in the form of an inhalation spray and do not react with the novel compounds, for example water, vegetable oils, benzyl alcohols, alkylene glycols, polyethylene glycols, glycerol triacetate, gelatine, carbohydrates, such as lactose or starch, magnesium stearate, talc, Vaseline. Suitable for oral use are, in particular, tablets, pills, dragees, capsules, powders, granules, syrups, juices or drops, suitable for rectal use are suppositories, suitable for parenteral use are solutions, preferably oily or aqueous solutions, furthermore suspensions, emulsions or implants, and suitable for topical use are ointments, creams or powders. The novel compounds may also be lyophilised and the resultant lyophilisates used, for example, for the preparation of injection preparations. The compositions indicated may have been sterilised and/or comprise adjuvants, such as lubricants, preservatives, stabilisers and/or wetting agents, emulsifiers, salts for modifying the osmotic pressure, buffer substances, dyes, flavours and/or a plurality of further active compounds, for example one or more vitamins.

For administration as inhalation spray, it is possible to use sprays which comprise the active compound either dissolved or suspended in a propellant gas or propellant-gas mixture (for example $CO_2$). The active compound here is advantageously used in micronised form, where one or more additional physiologically tolerated solvents may be present, for example ethanol. Inhalation solutions can be administered with the aid of conventional inhalers.

The substances according to the invention can generally be administered analogously to other, commercially available THC analogues, preferably in doses of between about 0.05 and 500 mg, in particular between 0.5 and 100 mg, per dosage unit. The daily dose is preferably between about 0.01 and 20 mg/kg of body weight. However, the specific dose for each patient depends on a very wide variety of factors, for example on the efficacy of the specific compound employed, on the age, body weight, general state of health, sex, on the diet, on the administration time and method, on the excretion rate, medicament combination and severity of the particular disease to which the therapy applies.

Furthermore, the novel compounds of the formula I can be used in analytical biology and molecular biology.

The following examples are intended to explain the invention without limiting it.

EXAMPLES 1. (6aR*,10aS*)-6,6-Difluoro-3-methyl-6a,7,8,9,10,10a-hexahydro-6H-benzo[c]chromen-1-ol 1.1 1-Hydroxy-3-pentyl-7,8,9,10-tetrahydrobenzo[c]chromen-6-one

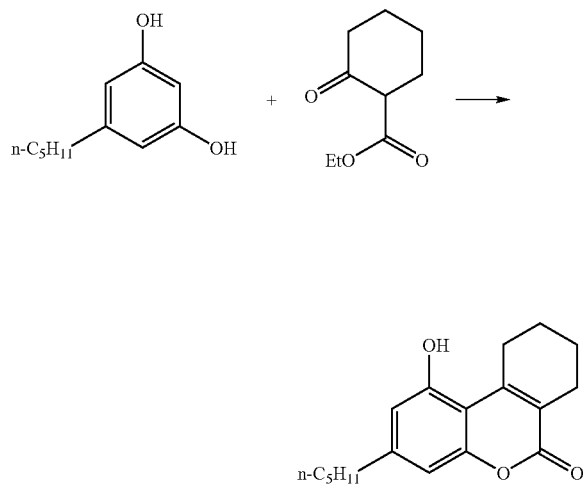

Olivetol (49.5 g, 261 mmol) and ethyl 2-oxocyclohexanecarboxylate (47.7 ml, 285 mmol) were initially introduced in toluene and, after addition of 28.8 ml (310 mmol) of phosphoryl chloride, were stirred at room temp. for 38 h. The reaction mixture was slowly poured into 400 ml of water and stirred vigorously for 30 min. The precipitated yellow solid was filtered off and washed with water and toluene. The pale-yellow solid was taken up in hot ethyl methyl ketone, washed with aqueous saturated sodium hydrogencarbonate soln. solution and sat. sodium chloride solution, dried over sodium sulfate, filtered and evaporated in vacuo. Crystallisation of the crude product from acetonitrile/toluene gave 32.7 g (82%) of 1-hydroxy-3-pentyl-7,8,9,10-tetra-hydrobenzo[c]chromen-6-one as colourless crystals.

1.2 1-tert-Butyldimethylsilyloxy-3-pentyl-7,8,9,10-tetrahydrobenzo[c]chromen-6-one

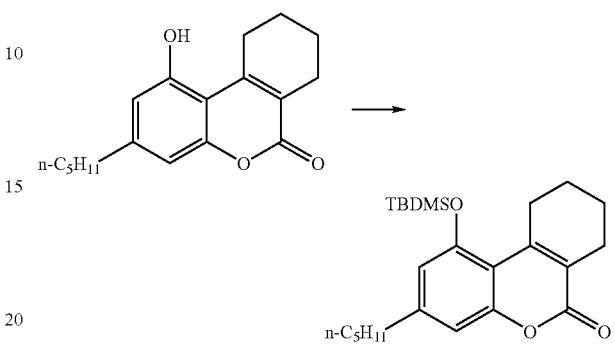

32 g (112 mmol) of 1-hydroxy-3-pentyl-7,8,9,10-tetrahydrobenzo[c]chromen-6-one were initially introduced in 200 ml of DMF, 10 g of imidazole (145 mmol) were added, a solution of 21 g (135 mmol) of tert-butyldimethyl-silyl chloride in 100 ml of DMF was added dropwise at 0° C., and the mixture was stirred at room temp. for 20 h. MTB ether was subsequently added to the batch, which was then washed with water and dried over sodium sulfate. The solvent was removed in vacuo, and the residue was purified by chromatography with heptane/ethyl acetate (6:1), giving 44.5 g (94%) of 1-tert-butyl-dimethylsilyloxy-3-pentyl-7,8,9,10-tetrahydrobenzo[c]chromen-6-one as a yellow solid.

1.3 (6aR*,10aS*)-1-tert-butyldimethylsilyloxy-3-pentyl-6a,7,8,9,10,10a-hexa-hydrobenzo[c]chromen-6-one

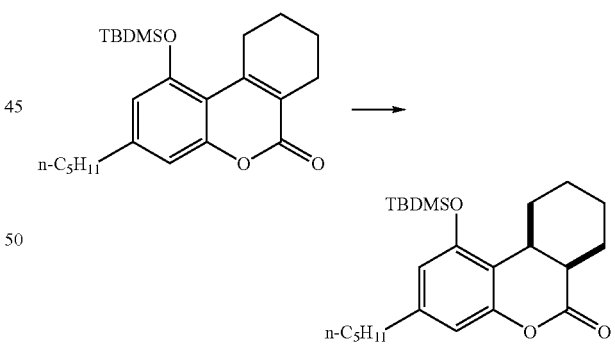

30 g (74.9 mmol) of 1-tert-butyldimethylsilyloxy-3-pentyl-7,8,9,10-tetrahydro-benzo[c]-chromen-6-one were hydrogenated to completion on palladium/carbon in THF. The catalyst was filtered off, the solvent was removed in vacuo, and the residue was filtered through silica gel with heptane/ethyl acetate (15:1), giving 24.5 g (81%) of (6aR*,10aS*)-1-tert-butyldimethylsilyloxy-3-pentyl-6a,7,8,9,10,10a-hexahydrobenzo[c]chromen-6-one as a colourless oil.

$^1$H-NMR (300 MHz, CDCl$_3$)

δ=6.47 ppm (d, $^4$J=1.3 Hz, 1H), 6.39 (d, $^4$J=1.3 Hz, 1H), 3.11 (ddd, J$_{cis}$=3.7 Hz, J$_{cis}$=5.8 Hz, J$_{trans}$=12.3 Hz, 1H), 2.87-2.82 (m, 1H), 2.50 (t, $^3$J=7.0 Hz, 2H), 1.82 (bt, $^3$J=6.0 Hz, 2H), 1.66-1.49 (m, 6H), 1.36-1.15 (m, 6H), 1.02 (s, 9H), 0.89 (t, $^3J$=7.0 Hz, 3H), 0.26 (s, 3H), 0.25 (s, 3H)

1.4. (6aR*, 10aS*)-6,6-difluoro-3-methyl-6a, 7,8,9, 10,10a-hexahydro-6H-benzo[c]chromen-1-ol

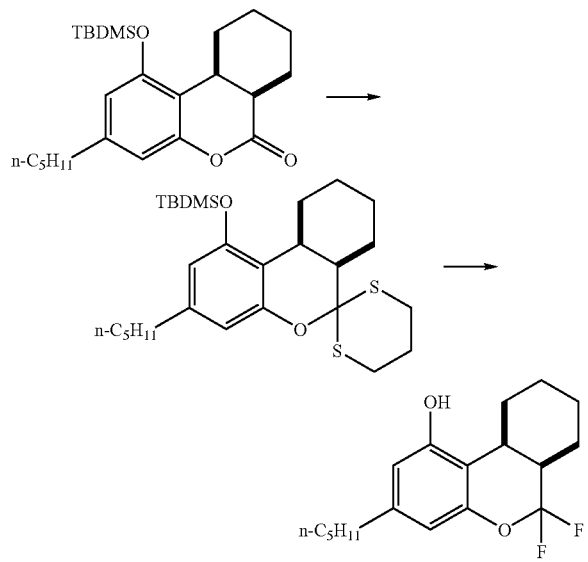

75 ml of dichloromethane were cooled to −78° C., trimethylaluminium (2 M, solution in hexane, 16.25 ml, 32.5 mmol) was added, and 1.57 ml (15.7 mmol) of 1,3-propanedithiol were slowly added dropwise. The batch was stirred for a further 5 min and then warmed to room temp. over the course of 30 min, left to stir for 30 min and re-cooled to −78° C. A solution of 5.6 g (13 mmol) of (6aR*,10aS*)-1-tert-butyldimethylsilyloxy-3-pentyl-6a,7,8,9,10,10a-hexahydrobenzo[c]chromen-6-one in 25 ml of dichloromethane was subsequently slowly added dropwise, the batch was left to thaw and stirred at room temp. for a further 18 h. After hydrolysis, the aqueous phase was extracted with dichloromethane, the combined organic extracts were dried over sodium sulfate and filtered. The solution was stirred for 2 h in the presence of 30 g of silica gel, filtered and evaporated. 17.7 g (62 mmol) of DBH was initially introduced in 150 ml of dichloromethane, 1.9 ml (62 mmol) of 60 percent HF/pyridine were added at −78° C., and the suspension was stirred at this temperature for 30 min. A solution of the dithiospiro compound obtained in the first step in 50 ml of dichloromethane was subsequently slowly added dropwise, and the mixture was stirred at −70° C. for 3.5 h. After hydrolysis using 10 percent sodium hydroxide solution, the batch was extracted with dichloromethane, washed with sat. sodium chloride soln. and dried over sodium sulfate.

The solvent was removed in vacuo, and the residue was chromatographed on silica gel with heptane/ethyl acetate (20:1). The resultant crude product was hydrogenated to completion in tetrahydrofuran/water 2:1 in the presence of triethylamine on palladium/activated carbon, filtered and washed with water. The aqueous phases were extracted with dichloromethane, and the combined org. phases were dried over sodium sulfate. The solvent was removed in vacuo, and the residue was chromatographed on silica gel with heptane/ethyl acetate (15:1), giving (6aR*,10aS*)-6,6-difluoro-3-pentyl-6a,7,8,9,10,10a-hexahydro-6H-benzo[c]chromen-1-ol as a colourless oil $^1$H-NMR (300 MHz, CDCl$_3$)
δ=6.39 (d, $^4J$=1.5 Hz, 1H), 6.22 (d, $^4J$=1.5 Hz, 1H), 4.73 (s,1H), 3.28-3.18 (m, 1H), 2.74 (bt, J=1.9 Hz, 1H), 2.46 (t, $^3J$=7.0 Hz, 2H), 2.17-2.10 (m, 1H), 1.93-1.83 (m, 3H), 1.61-1.25 (m, 10H), 0.89 (t, $^3J$=7.0 Hz, 3H)
$^{19}$F-NMR (235 MHz CDCl$_3$):
δ=−79.70 (dd, $^2J_{F,F}$=151.4 Hz, $^3J_{H,F}$=21.8 Hz, 1 F), −81.06 (d, $^2J_{F,F}$=151.4 Hz, 1 F)

2. (6aR*,10aS*)-3-(1,1-dimethylheptyl)-6,6-difluoro-6a,7,8,9,10,10a-hexa-hydro-6H-benzo[c]chromen-1-ol

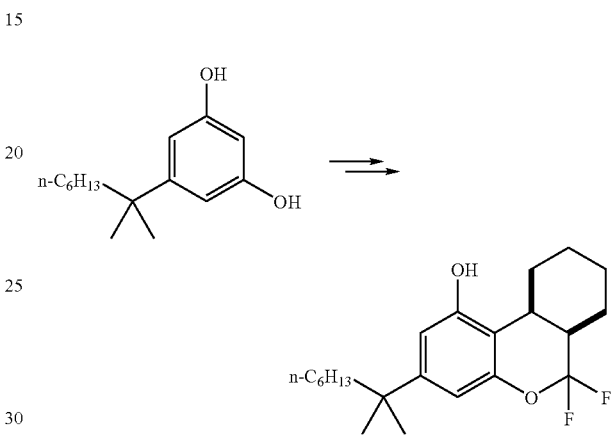

(6aR*,10aS*)-3-(1,1-Dimethylheptyl)-6,6-difluoro-6a,7,8,9,10,10a-hexahydro-6H-benzo[c]chromen-1-ol was obtained from 5-(1,1-dimethylheptyl)resorcinol analogously to the synthesis described under 1.1 to 1.3.
$^1$H-NMR (300 MHz, CDCl$_3$):
δ=6.51 ppm (d, $^4J$=1.8 Hz, 1H), 6.34 (d, $^4J$=1.8 Hz, 1H), 4.83 (s, 1H), 3.28-3.19 (m, 1H), 2.74 (bt, J=11.3 Hz, 1H), 2.17-2.10 (m, 1H), 1.94-1.81 (m, 4H), 1.55-1.36 (m, 8H), 1.25-1.15 (m, 8H), 1.12-1.01 (m, 3H), 0.85 (t, $^3J$=6.8 Hz, 3H)
$^{19}$F-NMR (235 MHz, CDCl$_3$):
δ=−79.7 (dd, $^2J_{F,F}$=152 Hz, $^3J_{H,F}$=22.4 Hz, 1 F), −81.1 (d, $^2J_{F,F}$=152 Hz, 1 F)

3. (6aR*,10aR*)-6,6-difluoro-3-pentyl-6a, 7,8,9,10, 10a-hexahydro-6H-benzo[c]chromen-1-ol

3.1 Methyl 2-(2,6-dimethoxy-4-pentylphenyl)cyclohexanecarboxylate

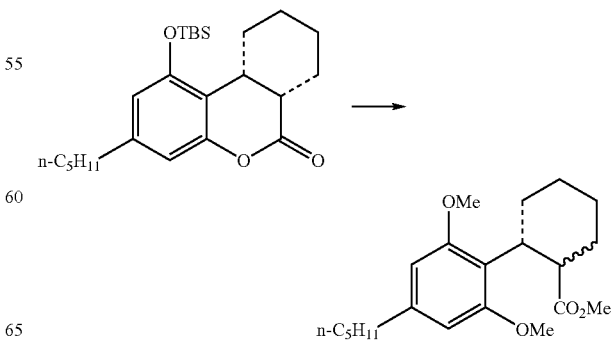

28.5 g (93.9 mmol) of 1-tert-butyldimethylsilyloxy-3-pentyl-6a,7,8,9,10,10a-hexahydrobenzo[c]chromen-6-one were dissolved in 600 ml of methanol and, after addition of 15.9 g (283 mmol) of potassium hydroxide, were heated under reflux for 3 h. The solvent was removed in vacuo, the residue was taken up in 450 ml of THF and 100 ml of DMPU and heated under reflux overnight in the presence of 5 equivalents of methyl iodide. After addition of 150 ml of water, the org. phase was separated off, and the aqueous phase was extracted three times with MTB ether. The combined org. phases were washed with water and dried over sodium sulfate. The solvent was removed in vacuo, and the residue was filtered through silica gel with heptane/ethyl acetate (8:1), giving 27.5 g (84%) of the diastereomeric methyl 2-(2,6-di-methoxy-4-pentylphenyl)cyclohexanecarboxylate as a yellow oil.

3.2 Methyl trans-2-(2,6-dimethoxy-4-pentylphenyl)cyclohexanecarboxylate

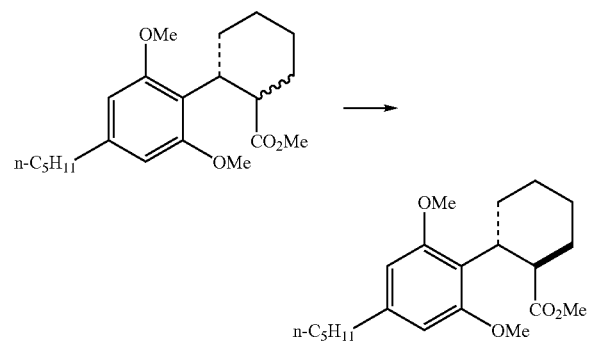

600 mg (1.7 mmol) of methyl 2-(2,6-dimethoxy-4-pentylphenyl)cyclohexane-carboxylate were dissolved in 10 ml of methanol, a solution of 200 mg (8.7 mmol) of sodium in 7.5 ml of methanol was added, and the mixture was heated under reflux overnight. The mixture was subsequently diluted with water, acidified using acetic acid and extracted with dichloromethane. The combined organic phases were dried over sodium sulfate, filtered and evaporated, giving 388 mg (75%) of methyl trans-2-(2,6-dimethoxy-4-pentyl-phenyl)cyclohexanecarboxylate as a colourless oil.

3.3 (6aR*,10aR*)-1-hydroxy-3-pentyl-6a,7,8,9,10,10a-hexahydrobenzo[c]-chromen-6-one

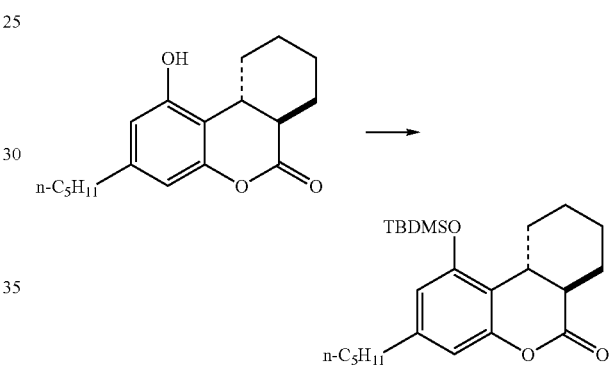

260 mg (0.75 mmol) of methyl trans-2-(2,6-dimethoxy-4-pentylphenyl)cyclo-hexanecarboxylate were initially introduced in 10 ml of dichloromethane, and 191 µl (2 mmol) of boron tribromide were added at −70° C. After 20 min, the cooling was removed, and the batch was hydrolysed at 0° C. using sat. sodium hydrogencarbonate soln. The mixture was extracted with dichloromethane, dried over sodium sulfate and evaporated. Chromatography with heptane/ethyl acetate (7:1) gave 100 mg (45%) of (6aR*,10aR*)-1-hydroxy-3-pentyl-6a,7,8,9,10,10a-hexahydrobenzo[c]chromen-6-one as a colourless solid.

$^1$H-NMR (300 MHz, CDCl$_3$):

δ=6.48 (d, $^4$J=1.6 Hz, 1H), 6.31 (d, $^4$J=1.6 Hz, 1H), 4.94 (s, 1H), 3.28-3.19 (m, 1H), 2.82 (dt, J$_{trans}$=12.4 Hz, J$_{cis}$=3.6 Hz 1H), 2.49 (t, $^3$J=7.0 Hz, 2H), 2.38-2.18 (m, 2H), 1.92-1.85 (m, 2H), 1.60-1.47 (m, 3H), 1.37-1.25 (m, 7H), 0.89 (t, $^3$J=7.0 Hz, 3H).

3.4. (6aR*,10aR*)-1-(tert-butyldimethylsilyloxy)-3-pentyl-6a,7,8,9,10,10a-hexahydrobenzo[c]chromen-6-one Reaction of (6aR*,10aR*)-1-hydroxy-3-pentyl-6a,7,8,9,10,10a-hexahydro-benzo[c]chromen-6-one corresponding to the synthesis described under 1.2 gave (6aR*,10aR*)-1-(tert-butyldimethylsilyloxy)-3-pentyl-6a,7,8,9,10,10a-hexahydrobenzo[c]chromen-6-one as a colourless oil.

3.5 (6aR*, 10aR*)-1-(tert-butyldimethylsilyloxy)-3-pentyl-6a,7,8,9,10,10a-hexahydrobenzo[c]chromene-6-thione

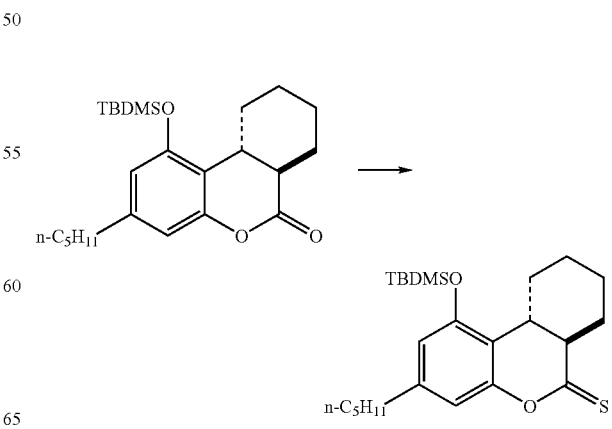

2.00 g (4.97 mmol) of (6aR*,10aR*)-1-(tert-butyldimethylsilyloxy)-3-pentyl-6a,7,8,9,10,10a-hexahydrobenzo[c]chromen-6-one was heated under reflux at 140° C. for 17 h with 4.25 g (10.2 mmol) of Lawesson's reagent in xylene.

The solvent was removed in vacuo, and the residue was chromatographed on silica gel with heptane/ethyl acetate (20:1), giving (6aR*,10aR*)-1-(tert-butyldimethylsilyloxy)-3-pentyl-6a,7,8,9,10,10a-hexahydrobenzo[c]-chromene-6-thione as a yellow oil.

$^1$H-NMR (300 MHz, CDCl$_3$):

δ=6.60 (d, $^4$J=1.3 Hz, 1H), 6.43 (d, $^4$J=1.3 Hz, 1H), 3.08 (ddd, J$_{cis}$=3.5 Hz, J$_{cis}$=5.8 Hz, J$_{trans}$=12.2 Hz, 1H), 2.86-2.80 (m, 2H), 2.52 (t, $^3$J=7.0 Hz, 2H), 1.87-1.70 (m, 4H), 1.61-1.53 (m, 3H), 1.36-1.25 (m, 6H), 1.02 (s, 9H), 0.89 (t, $^3$J=7.0 Hz, 3H), 0.26 (s, 3H), 0.25 (s, 3H).

3.6 (6aR*,10aR*)-6,6-difluoro-3-pentyl-6a,7,8,9,10,10a-hexahydro-6H-benzo[c]chromen-1-ol

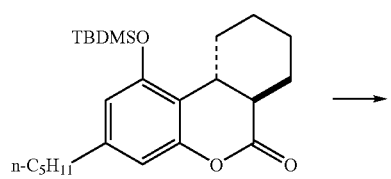

500 mg (1.19 mmol) of (6aR*,10aR*)-1-(tert-butyldimethylsilyloxy)-3-pentyl-6a,7,8,9,10,10a-hexahydrobenzo[c]chromene-6-thione were dissolved in 10 ml of dichloromethane, and 0.4 ml (3 mmol) of DAST was added with ice-cooling. The cooling was removed, and the batch was left to stir overnight at room temp. The batch was subsequently added to sat. sodium hydrogen-carbonate soln. and extracted three times with MTB ether. The combined org. phases were washed with water and dried over sodium sulfate. The solvent was removed in vacuo, and the residue was chromatographed on silica gel with heptane/ethyl acetate (15:1), giving (6aR*,10aR*)-6,6-difluoro-3-pentyl-6a,7,8,9,10,10a-hexahydro-6H-benzo[c]chromen-1-ol as a colourless oil 4. (6aR*,10aS*)-6,6-difluoro-1-hydroxy-3-pentyl-6,6a,7,8,10,10a-hexa-hydrobenzo[c]chromen-9-one 4.1-1-(tert-Butyldimethylsilyl)-3-pentyl-7,10-dihydro-8H-benzo[c]chromene-6,9-dione 9-ethylene ketal

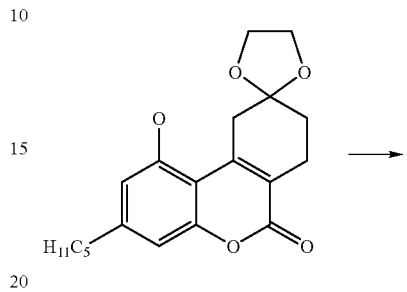

1-(tert-Butyldimethylsilyloxy)-3-pentyl-7,10-dihydro-8H-benzo[c]chromene-6,9-dione 9-ethylene ketal was obtained from -1-hydroxy-3-pentyl-7,10-di-hydro-8H-benzo[c]chromene-6,9-dione 9-ethylene ketal [prepared by the method of R. A. Archer, W. B. Blanchard, W. A. Day, D. W. Johnson, E. R. Lavagnino, C. W. Ryan, *J. Org. Chem.* 1977, 42, 2277-2284] and tert-butyl-dimethylsilyl chloride analogously to the synthesis described under 1.2.

4.2 (6aR*,10aS*)-1-(tert-butyldimethylsilyloxy)-3-pentyl-7,8,10,10a-tetra-hydro-6aH-benzo[c]chromene-6,9-dione ethylene ketal

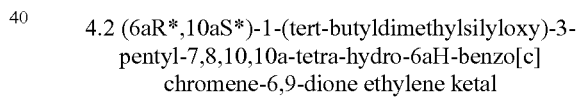

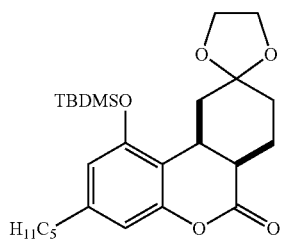

Hydrogenation of 1-(tert-butyldimethylsilyloxy)-3-pentyl-7,10-dihydro-8H-benzo[c]chromene-6,9-dione 9-ethylene ketal on palladium/activated carbon analogously to the synthesis described under 1.3 gave (6aR*,10aS*)-1-(tert-butyldimethylsilyloxy)-3-pentyl-7,8,10,10a-tetrahydro-6aH-benzo[c]chromene-6,9-dione 9-ethylene ketal.

4.3 (6aR*,10aS*)-1-(tert-butyldimethylsilyloxy)-3-pentyl-7,8,10,10a-tetra-hydro-6aH-benzo[c]chromene-6,9-dione 6-propylene dithioketal 9-ethylene ketal

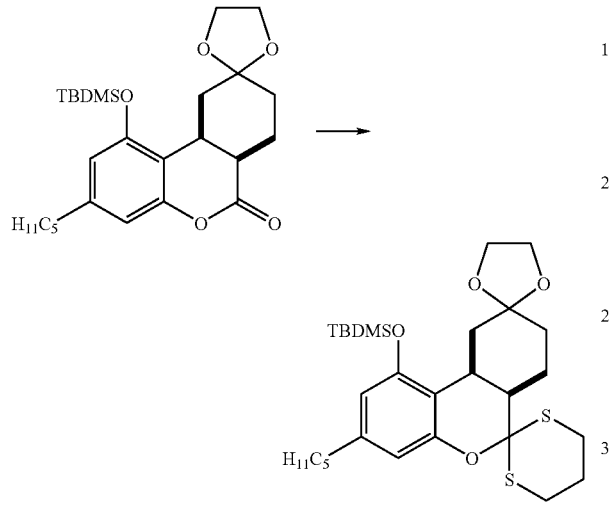

150 ml of dichloromethane were cooled to −78° C., 26 ml (51 mmol) of a 2 M solution of trimethylaluminium in hexane were added, and 2.5 ml (25 mmol) of 1,3-propanedithiol were slowly added dropwise. The batch was stirred for a further 5 min and then warmed to room temp. over the course of 30 min, left to stir for 30 min and re-cooled to −78° C. A solution of 9.9 g (21 mmol) of (6aR*,10aS*)-1-(tert-butyldimethylsilyloxy)-3-pentyl-7,8,10,10a-tetrahydro-6aH-benzo[c]chromene-6,9-dione 9-ethylene ketal in 50 ml of dichloromethane was subsequently slowly added dropwise, the batch was left to thaw and stirred at room temp. for a further 18 h. After hydrolysis, the aqueous phase was extracted with dichloromethane, and the combined organic phases were dried over sodium sulfate. The solvent was removed in vacuo, the residue was dissolved in dichloromethane and stirred for 2 min presence of 350 mg of pyridinium p-toluenesulfonate. The solution was washed with water, and the aqueous phase was extracted with dichloromethane. The combined organic phases were washed with sat. sodium hydrogencarbonate soln., dried over sodium sulfate, filtered and evaporated. Chromatography on silica gel with heptane/ethyl acetate (8:1, 3:1) gave (6aR*,10aS*)-1-(tert-butyldimethylsilyloxy)-3-pentyl-7,8,10,10a-tetrahydro-6aH-benzo[c]chromene-6,9-dione 6-propylene dithioketal 9-ethylene ketal as a colourless oil.

$^1$H-NMR (300 MHz, CDCl$_3$):

δ=6.32 (d, $^4$J=1.1 Hz, 1H), 6.21 (d, $^4$J=1.1 Hz, 1H), 3.82-3.73 (m, 4H), 3.01-2.97 (m, 1H), 2.93-2.85 (m, 3H), 2.44 (t, $^3$J=7.0 Hz, 2H), 2.25-2.20 (m, 2H), 2.15-2.11 (m, 2H), 1.99 (dt, J=14.0 Hz, J=5.2 Hz, 1H), 1.86 (dd, J=12.2 Hz, J=3.0 Hz, 1H), 1.72 (dt, J=14.0 Hz, J=5.2 Hz, 1H), 1.58-1.52 (m, 5H), 1.34-1.25 (m, 4H), 0.96 (s, 9H), 0.88 (t, $^3$J=7.0 Hz, 3H), 0.35 (s, 3H), 0.27 (s, 3H).

4.4 (6aR*,10aS*)-6,6-difluoro-1-hydroxy-3-pentyl-6,6a,7,8,10,10a-hexa-hydrobenzo[c]chromen-9-one

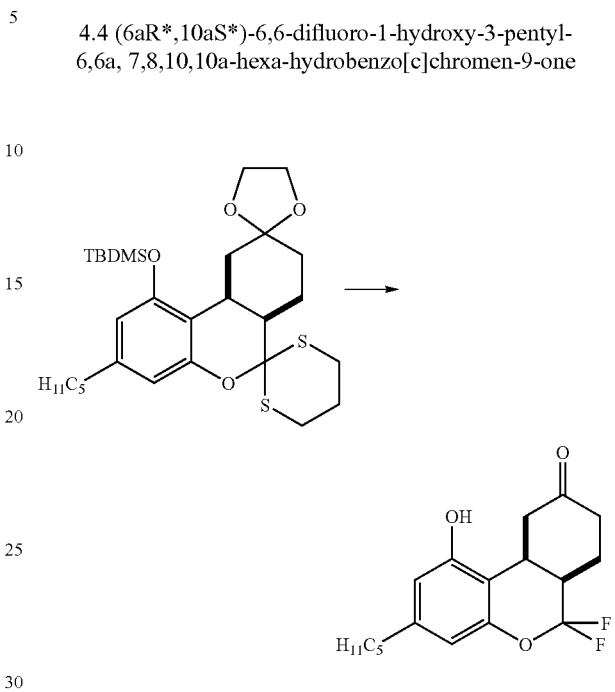

1.82 g (3.30 mmol) of the thio compound obtained in 4.3 were added at −78° C. to a suspension of 3.35 g (14.6 mmol) of N-iodosuccinimide in 100 ml of dichloromethane and 0.6 ml (21 mmol) of 70 percent HF/pyridine complex, left to stir for 3 h and subsequently added to a mixture of 100 ml of 10 percent sodium hydroxide solution and 20 ml of sat. sodium hydrogensulfite soln. The aqueous phase was separated off and extracted with dichloromethane. The combined org. phases were washed with sat. sodium chloride soln. and dried over sodium sulfate. The solvent was removed in vacuo, the residue was dissolved in acetone and left to stir at room temp. for 24 h in the presence of p-toluenesulfonic acid. The solution was neutralised using sodium hydroxide solution, and the solvent was removed in vacuo. Chromatography of the crude product on silica gel with heptane/ethyl acetate (3:1) gave (6aR*,10aS*)-6,6-difluoro-1-hydroxy-3-pentyl-6,6a,7,8,10,10a-hexahydrobenzo[c]chromen-9-one as a yellow oil.

$^{19}$F-NMR (235 MHz, CDCl$_3$):

δ=−81.0 ppm ($^2$J=152 Hz, 1 F), −82.5 ($^2$J=152 Hz, $^3$J=20 Hz, 1 F).

The specific ligand binding to the receptors is defined as the difference between complete binding and non-specific binding determined in the presence of an excess of unlabelled ligand (see, for example, MUNRO, S., THOMAS, K. L. and ABU-SHAAR, M. (1993), Molecular characterisation of a peripheral receptor for cannabinoids.

*Nature,* 365:61-65. RINALDI-CARMONA, M., CALANDRA, B., SHIRE, D., BOUABOULA, M., OUSTRIC, D., BARTH, F., CASELLAS, P., FERRARA, P. and LE FUR, G. (1996), Characterisation of two cloned human CB$_1$ cannabinoid receptors isoform; *J. Pharmacol. Exp. Ther.,* 278: 871-878.

These results are expressed as a percentage of the specific comparative binding in the presence of test substance Ia.

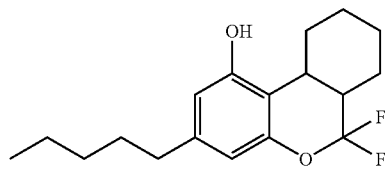

The $IC_{50}$ values (concentration necessary for half-maximum inhibition of the specific control binding) and Hill coefficients ($n_H$) are obtained by non-linear regression analyses of the competition curves, with the curve matching being carried out in accordance with the Hill equation.

The inhibition constants ($K_i$) are calculated in accordance with the Cheng Prusoff equation ($K_i = IC_{50}/1+(L/K_D)$).

The $IC_{50}$ and $K_i$ values determined for compound Ia are shown in Table 1 below.

TABLE 1

| Assay | Ligand | $IC_{50}$ (M) | $K_i$ (M) | $n_H$ |
|---|---|---|---|---|
| CB1 (h) | Compound Ia | 2.2E−06 | 1.9E−06 | 1.5 |
| CB2 (h) | Compound Ia | 1.4E−06 | 9.2E−07 | 0.9 |

The data of the comparative substances are shown in the table below.

TABLE 2

| Assay | Ligand | $IC_{50}$ (M) | $K_i$ (M) | $n_H$ |
|---|---|---|---|---|
| CB1 (h) | CP55940 | 2.2E−09 | 1.9E−09 | 1.1 |
| CB2 (h) | WIN55212-2 | 1.4E−09 | 9.2E−09 | 0.7 |

The competition curves obtained with compound Ia are shown in FIGS. 1 and 2.

Figure 1:
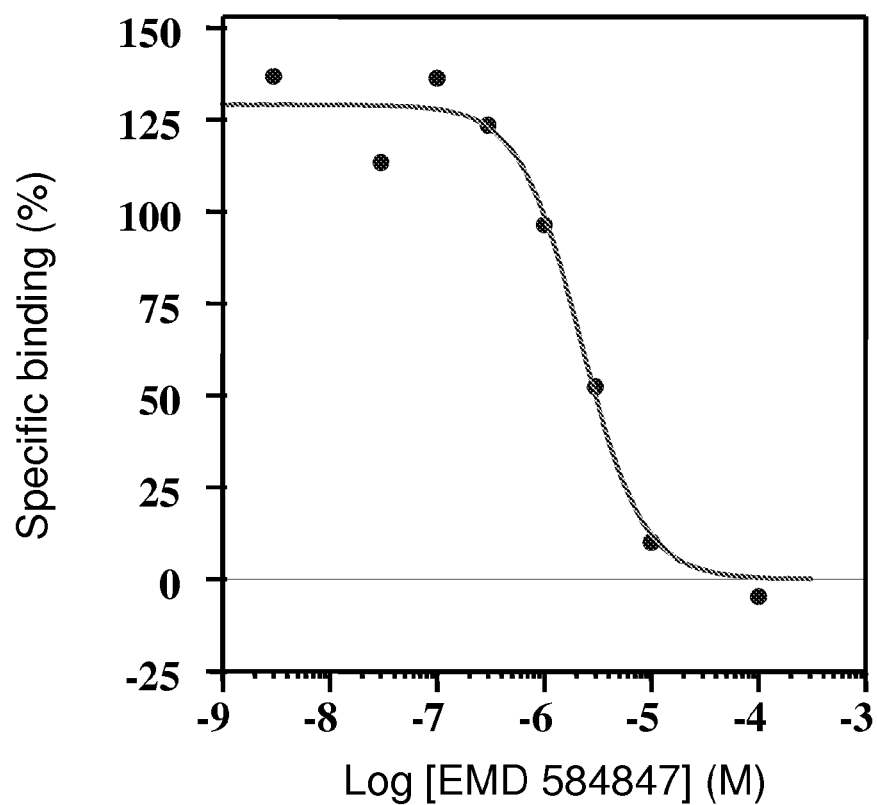
FIG. 1 illustrates a competition curve obtained with compound Ia on human CB1 receptor.
Figure 2:
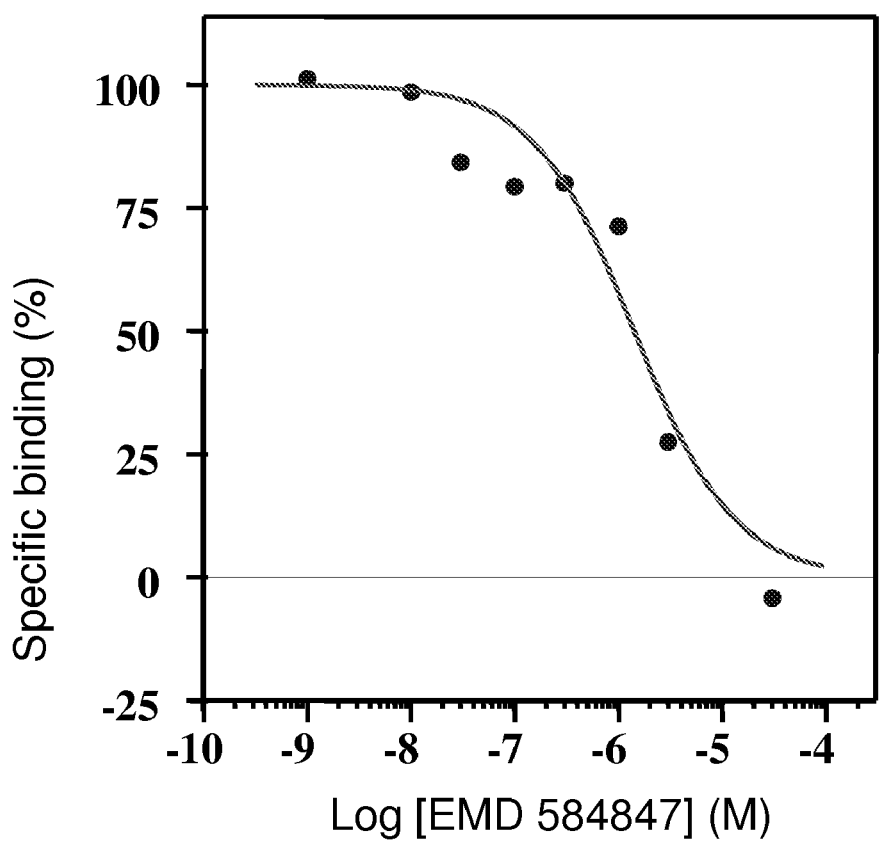
FIG. 2 illustrates a competition curve obtained with compound Ia on human CB2 receptor.

The following examples relate to pharmaceutical compositions:

Example A

Injection Vials

A solution of 100 g of an active compound of the formula I and 5 g of di-sodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

Example B

Suppositories

A mixture of 20 g of an active compound of the formula I with 100 g of soya lecithin and 1400 g of cocoa butter is melted, poured into moulds and allowed to cool. Each suppository contains 20 mg of active compound.

Example C

Solution

A solution is prepared from 1 g of an active compound of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active compound of the formula I are mixed with 99.5 g of Vaseline under aseptic conditions.

Example E

Tablets

A mixture of 1 kg of active compound of the formula I, 4 kg of lactose, 1.2 kg of potato starch, 0.2 kg of talc and 0.1 kg of magnesium stearate is pressed to give tablets in a conventional manner in such a way that each tablet contains 10 mg of active compound.

Example F

Dragees

Tablets are pressed analogously to Example E and subsequently coated in a conventional manner with a coating of sucrose, potato starch, talc, tragacanth and dye.

Example G

Capsules 2 kg of active compound of the formula I are introduced into hard gelatine capsules in a conventional manner in such a way that each capsule contains 20 mg of the active compound.

Example H

Ampoules

A solution of 1 kg of active compound of the formula I in 60 l of bidistilled water is sterile filtered, transferred into ampoules, lyophilised under sterile conditions and sealed under sterile conditions. Each ampoule contains 10 mg of active compound.

Example I

Inhalation Spray 14 g of active compound of the formula I are dissolved in 10 l of isotonic NaCl solution, and the solution is introduced into commercially available spray vessels with a pump

The invention claimed is:

1. A compound of formula I

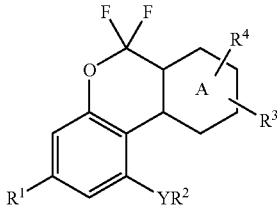

in which
A denotes a saturated or partially unsaturated carbocyclic or heterocyclic radical having 6 ring members, in which, in the case of saturated radicals, one or more $CH_2$ groups may be replaced by CO,
$R^1$, $R^2$,
$R^3$, and $R^4$ independently of one another, denote H, Hal, branched or unbranched alkyl having 1 to 12 C atoms, in which one or more H atoms may be replaced by F, one or more $CH_2$ groups may be replaced by —C=C—, —C≡C—, C=O, —O—, —S—, —NH—, —N-alkyl- or substituted or unsubstituted phenylene, and one or more $CH_3$ groups may be replaced by

in which z denotes $CHR^5$, S, O, or $NR^5$,
Hal denotes fluorine, chlorine, bromine or iodine,
Y denotes O, S or $NR^5$;
$R^5$ denotes H or alkyl,
or a pharmaceutically acceptable salt or solvate thereof, or an isolated stereoisomer thereof or a mixture thereof.

2. A compound according to claim 1, in which $R^1$ denotes alkyl.

3. A compound according to claim 1, in which $R^3$ and/or $R^4$ denotes H, OH, alkyl or alkoxy.

4. A compound according to claim 1, in which Y denotes O.

5. A compound according to claim 1, in which $R^2$ denotes H, alkyl or

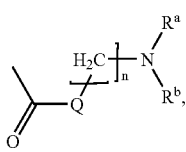

in which
n denotes 1, 2, 3, 4, 5, 6, 7, 8, 9, 10, 11 or 12
Q denotes O, NH, N-alkyl or $CH_2$,
$R^a$, $R^b$ independently denote H or alkyl
or the $NR^aR^b$ group together also denotes

in which
z denotes $CH_2$, S, O, $NR^1$ or NH.

6. A compound according to claim 5, in which Q denotes O.

7. A compound according to claim 5, in which the $NR^aR^b$ group denotes

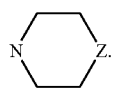

8. A compound selected from the group consisting of compounds of formulae I1 to I39 and Ia:

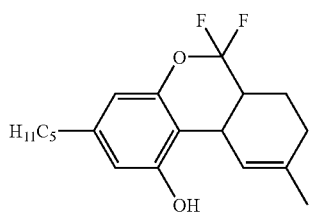

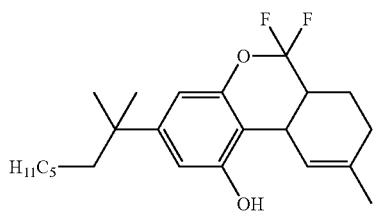

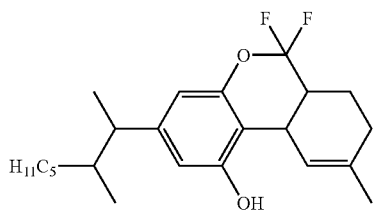

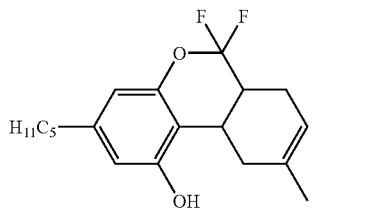

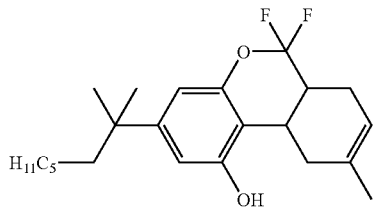

31
-continued
I6
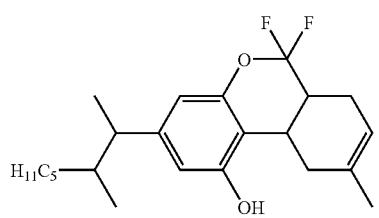
I7
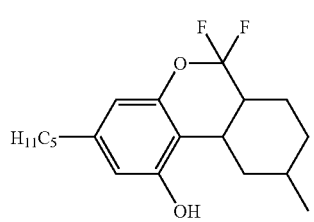
I8
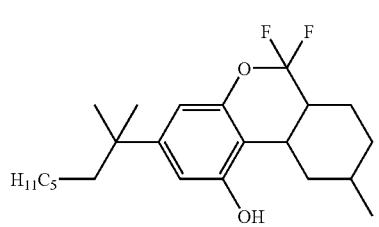
I9
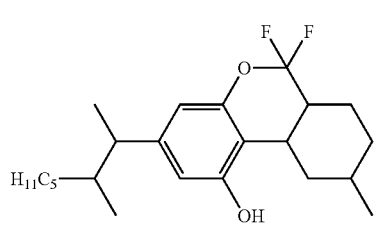
I10
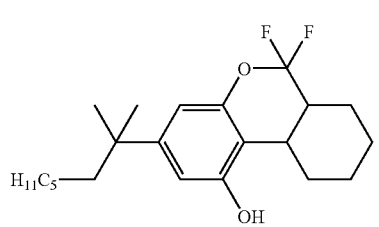
I11
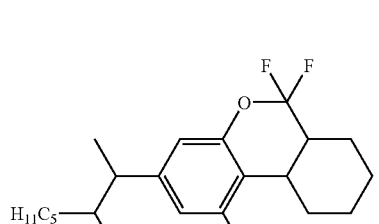
I12
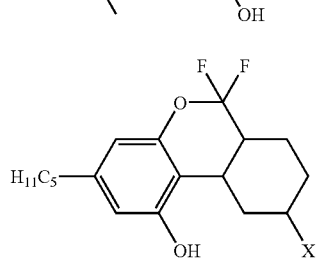
32
-continued
I13
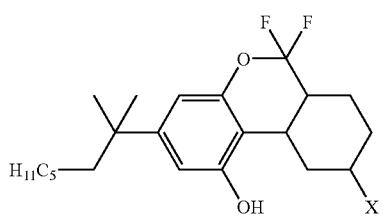
I14
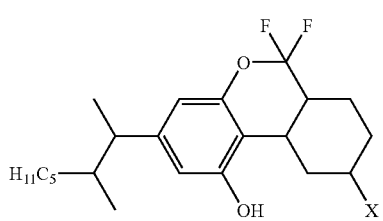
I15
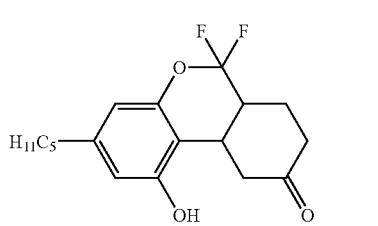
I16
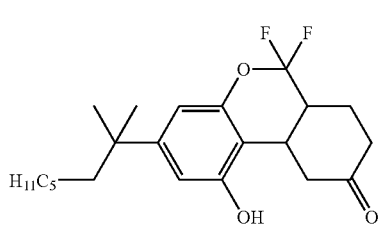
I17
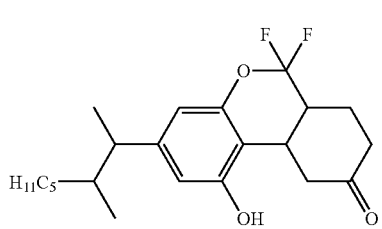
I18
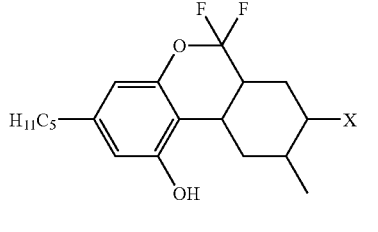
I19
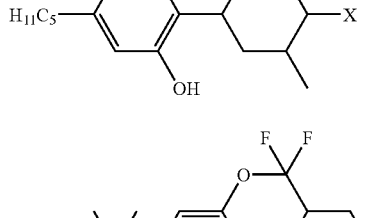

33
-continued
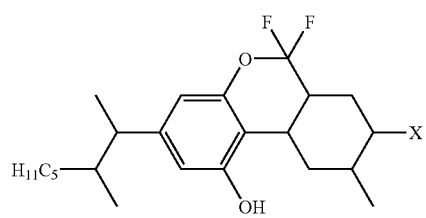
I20
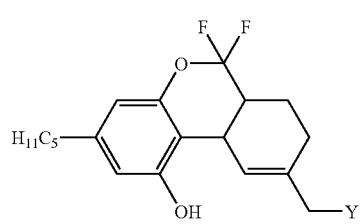
I21
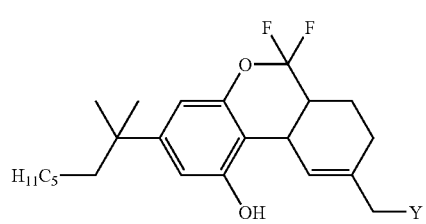
I22
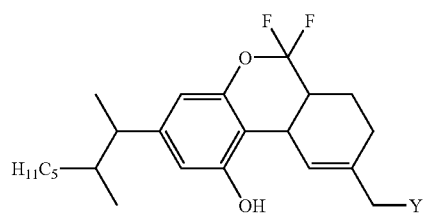
I23
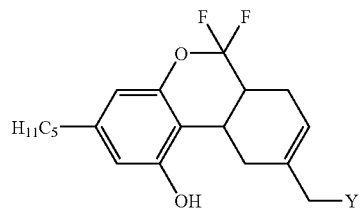
I24
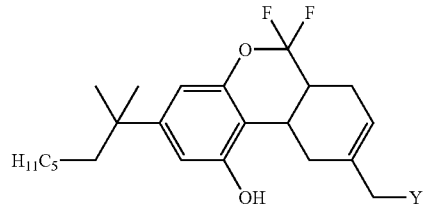
I25
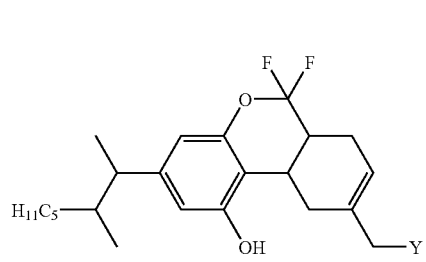
I26
34
-continued
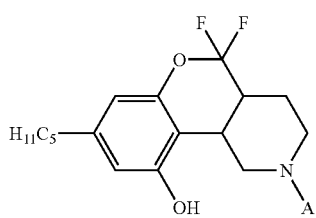
I27
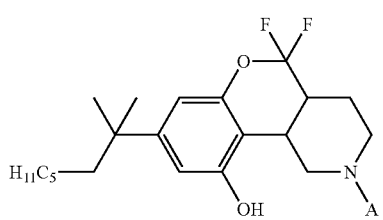
I28
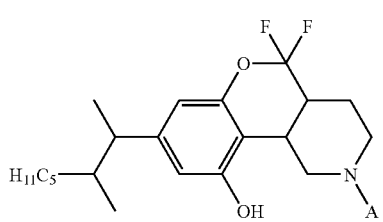
I29
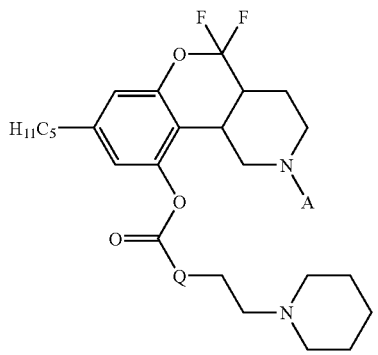
I30
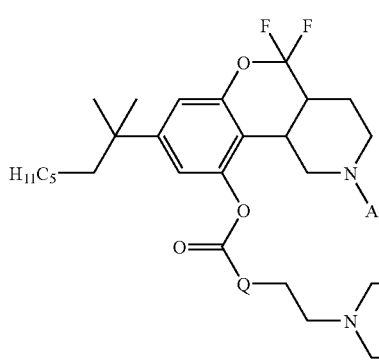
I31

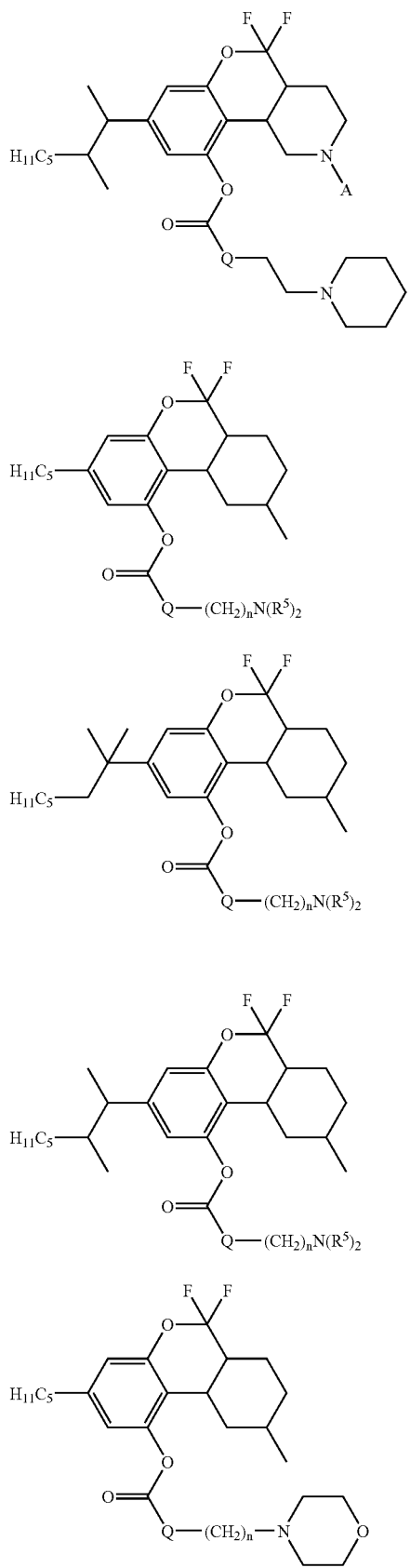

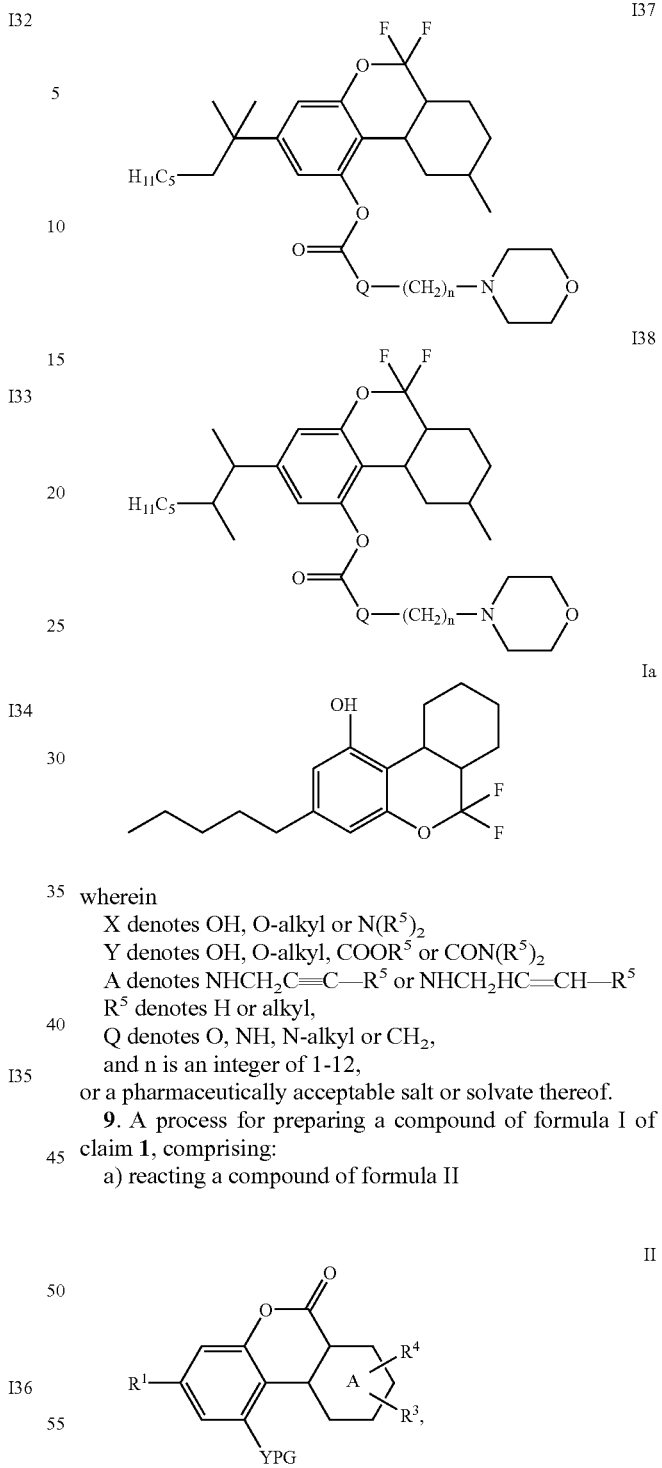

wherein
X denotes OH, O-alkyl or $N(R^5)_2$
Y denotes OH, O-alkyl, $COOR^5$ or $CON(R^5)_2$
A denotes $NHCH_2C\equiv C-R^5$ or $NHCH_2HC=CH-R^5$
$R^5$ denotes H or alkyl,
Q denotes O, NH, N-alkyl or $CH_2$,
and n is an integer of 1-12,
or a pharmaceutically acceptable salt or solvate thereof.

9. A process for preparing a compound of formula I of claim 1, comprising:
a) reacting a compound of formula II with aa) a thionation reagent or Lawesson's reagent, or ab) with a compound of formula $(alkyl)_2Al-S-(CH_2)_m-S-Al(alkyl)_2$, in which m denotes 2 or 3; and
subjecting the compounds obtained in aa) or ab) to oxidative fluorination with an oxidant which liberates a halonium equivalent or 1,3-dibromo-5,5-dimethylhydantoin or N-iodosuccinimide, in the presence of a fluoride source or triethylamine*3HF, or reacting the thionolactones obtained in ab) with a fluorinating reagent or diethylaminosulfur trifluoride or bis(2-methoxyethyl) aminosulfur trifluoride, and subsequently deprotecting to give the compound of formula I.

10. A process for preparing a compound of formula I of claim 1, comprising
a) reacting a compound of formula III

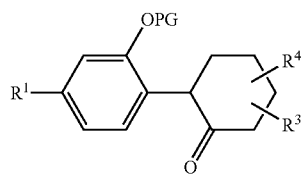

III in which $R^1$, $R^3$, and $R^4$ have the meaning as in the compound of formula I,
with a compound of the following formula

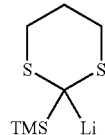

subjecting the compounds obtained in a) to oxidative fluorination with an oxidant which liberates halonium a halonium equivalent or 1,3-dibromo-5,5-dimethylhydantoin (DBH) or N-iodosuccinimide, in the presence of a fluoride source or triethyl-amine*3HF, and subsequently deprotecting to give the compound of formula I.

11. A method for inhibiting cannabinoid receptors, comprising administering to a subject in need thereof an effective amount of a compound of claim 1.

12. A pharmaceutical composition comprising at least one compound according to claim 1 and a pharmaceutically acceptable carrier.

13. A method for the treatment or prophylaxis of diseases or symptoms which can be influenced by the inhibition of cannabinoid receptors, comprising administering to a patient in need thereof an effective amount of a compound according to claim 1.

14. A method for treating a disease or disorder selected from the group consisting of psychoses, anxiety disorders, depression, aprosexia, memory disorders, cognitive disorders, loss of appetite, obesity, addiction, drug dependence, neurological disorders, neurodegenerative processes, dementia, dystonia, muscle spasms, tremor, epilepsy, multiple sclerosis, traumatic brain injuries, strokes, Parkinson's disease, Alzheimer's disease, Huntington's disease, Tourette's syndrome, cerebral ischaemia, cerebral apoplexy, craniocerebral trauma, spinal cord injuries, neuroinflammatory diseases, cerebral arteriosclerosis, viral encephalitis, diseases associated with demyelinisation, pain diseases, neuropathic pain diseases, diseases in which cannabinoid neurotransmission plays a role, septic shock, glaucoma, cancer, diabetes, vomiting, nausea, asthma, respiratory tract diseases, gastrointestinal diseases, gastric ulcer, diarrhoea, cardiovascular diseases, comprising administering to a patient in need thereof an effective amount of a compound according to claim 1.

15. A compound according to claim 1, or a pharmaceutically acceptable salt thereof.

16. A compound according to claim 8, or a pharmaceutically acceptable salt thereof.

17. A compound according to claim 1, in which —$YR^2$ denotes OH.

18. A compound according to claim 5, in which Y denotes O.

* * * * *